United States Patent [19]

Sung

[11] 4,431,430
[45] Feb. 14, 1984

[54] COMPOSITION CONTAINING A WATER SOLUBLE ALCOHOL AND A CORROSION INHIBITING ADDITIVE

[75] Inventor: Rodney L. Sung, Fishkill, N.Y.

[73] Assignee: Texaco Inc., White Plains, N.Y.

[21] Appl. No.: 206,815

[22] Filed: Nov. 14, 1980

[51] Int. Cl.³ .............................................. C10L 1/18
[52] U.S. Cl. ......................................... 44/53; 44/56; 44/63; 44/70
[58] Field of Search ............. 44/56, 53, 63, 70, 56 D; 252/396, 77, 56 D

[56] References Cited

U.S. PATENT DOCUMENTS

| | | | |
|---|---|---|---|
| 2,779,740 | 1/1957 | Messina | 252/51.5 A |
| 3,004,923 | 10/1961 | Jursich | 44/70 |
| 3,447,918 | 6/1969 | Amick | 252/396 |
| 3,927,041 | 12/1975 | Cengel et al. | 44/70 |
| 4,208,190 | 6/1980 | Malec | 44/53 |
| 4,242,099 | 12/1980 | Malec | 44/53 |

*Primary Examiner*—Charles F. Warren
*Assistant Examiner*—Y. Harris-Smith
*Attorney, Agent, or Firm*—Carl G. Ries; Robert A. Kulason; Carl G. Seutter

[57] ABSTRACT

Alcohols may be inhibited against corrosion by addition thereto of an alkenyl-substituted aliphatic dicarboxylic acid.

15 Claims, No Drawings

4,431,430

COMPOSITION CONTAINING A WATER SOLUBLE ALCOHOL AND A CORROSION INHIBITING ADDITIVE

FIELD OF THE INVENTION

This invention relates to alcohol products particularly characterized by decreased ability to corrode metal surfaces with which they come into contact.

BACKGROUND OF THE INVENTION

As is well known to those skilled in the art, alcohols such as ethanol may corrode metal surfaces with which they come into contact. This is particularly true of crude or commercially available ethanols which undesirably contain acidic components commonly acetic acid. In the case of fermentation alcohols, acetic acid may be present in amount of 0.003 w %–0.005 w % of the alcohol; and this may be responsible for the fact that the alcohol causes serious corrosion problems.

It is an object of this invention to provide a novel process for decreasing the corrosion of alcohol compositions. Other objects will be apparent to those skilled in the art.

STATEMENT OF THE INVENTION

In accordance with certain of its aspects, the novel composition of this invention may comprise (i) a water-soluble alcohol preferably selected from the group consisting of ethanol and methanol; and (ii) an effective anti-corrosion inhibiting amount of as corrosion-inhibiting agent an alkenyl-substituted aliphatic dicarboxylic acid, said alkenyl group having a molecular weight $\overline{M}_n$ of at least about 300.

DESCRIPTION OF THE INVENTION

The alcohol compositions which may be treated by the process of this invention may include $C_1$–$C_{12}$ alkanols such as water-soluble alkanols including $C_1$–$C_4$ alcohols. Preferably, the alcohols include methanol, ethanol, propanols, etc. The alcohols may include mixtures of alcohols with each other and/or with other compositions including ketones, esters, hydrocarbons, etc. The alcohol may be in the form of gasohol—a mixture commonly containing 80 v %–95 v %, say 90 v % gasoline and 5 v %–20 v %, say 10 v % alcohol. The alcohol may contain water, for example up to 10 w %–20 w %, typically 5 w %; but preferably it will be anhydrous. Anhydrous compositions commonly contain less than about 0.3 v % water, typically 0.001 v %–0.005 v %, say about 0.004 v % water. One preferred charge may be 100% anhydrous ethanol. Another preferred charge may be 100% anhydrous methanol.

Commercially available mixtures may be employed. Illustrative of one such commercially available mixture may be that having the following typical analysis:

TABLE I

| Component | Parts |
| --- | --- |
| ethanol | 3157.2 |
| methyl isobutyl ketone | 126.3 |
| acetic acid | 0.256 |
| methyl alcohol | 0.24 |
| isopropyl alcohol | 0.2 |
| n-propyl alcohol | 0.162 |
| ethyl acetate | 0.2 |

It is a particular feature of the process of this invention that it may be used to treat such compositions when they are to be used as fuels.

The fuels which may be treated by the process of this invention include gasohols which may be formed by mixing 90–95 volumes of gasoline with 5–10 volumes of ethanol or methanol. A typical gasohol may contain 90 volumes of gasoline and 10 volumes of absolute ethanol.

The fuels to be treated by the process of this invention may be substantially anhydrous i.e. they contain less than about 0.3 v % water; typically they may contain 0.001 v %–0.005 v %, say about 0.004 v % water.

It is a feature of these fuels that they may undesirably contain acidic contaminants which may cause serious corrosion problems. These contaminants are particularly in evidence when the alcohol is a commercially available alcohol which contains therein inter alia acids concurrently produced as by fermentation processes for producing ethanol or acids which have been picked up during handling. Acetic acid is a common acid present in the commercially available alcohols produced by fermentation; and it may be present in amount of 0.003 w %–0.005 w % of the total of the alcohol.

In accordance with practice of the process of this invention, there may be added to the alcohol a minor effective corrosion-inhibiting amount of, as a corrosion inhibiting agent at least one alkenyl-substituted aliphatic dicarboxylic acid, said alkenyl group having a molecular weight $\overline{M}_n$ of at least about 300.

The alkenyl-substituted aliphatic dicarboxylic acid, which may be used in practice of this invention, may be commercially available or they may be prepared by reaction of an unsaturated aliphatic dicarboxylic acid anhydride with an olefin oligomer or polyolefin reactant.

The unsaturated aliphatic dicarboxylic acid anhydrides which may be employed to form the desired alkenyl-substituted saturated aliphatic dicarboxylic acids in practice of this invention may be intramolecular anhydrides typified by the following:

TABLE

| maleic | anhydride |
| citraconic | anhydride |
| itaconic | anhydride |
| ethylmaleic | anhydride |
| halo (eq chloromaleic) | anhydride |
| glutaconic | anhydride |
| homeosaconic | anhydride, etc. |

The preferred anhydride may be maleic anhydride.

The olefin oligomer, or polyolefin, reactant which may be employed may typically be an oligomer of a $C_2$–$C_8$ olefin having a molecular weight $\overline{M}_n$ of greater than about 300, and preferably about 300–30,000, more commonly about 300–3000, say 1050–1400. The preferred oligomers are the polyisobutylenes, more preferably polyisobutylene of $\overline{M}_n$ of 300–5000, say 300–3000.

The polybutenes which may be employed may include those polymers obtained by polymerizing refinery streams containing eg isobutylenes, cis-butene-2,trans-butene-2, and butene-1. Polymerization of such streams, typically by use of a Friedel-Crafts catalyst, permits attainment of a polyisobutylene of $\overline{M}_n$ of 300–5000, preferably 500–2000, say 700–1500, typically 1050–1400, and a viscosity of 4–5500 centistokes at 100° C. Molecular weight $\overline{M}_n$ may be determined by ASTM D-2503 method.

Reaction between the polyolefin and the unsaturated aliphatic dicarboxylic acid anhydride to form the alkenyl saturated aliphatic dicarboxylic acid anhydride may be carried out at 150° C.–300° C. preferably about 210° C.–245° C., say about 245° C. for 2–10, preferably 4–10, say 6 hours at autogenous pressures in batch operation or at 150° C.–300° C., preferably 210° C.–245° C., say about 245° C. for 1–3 hours in a continuous process.

The reaction may be carried out in the presence of a catalyst such as brominated dialkylhydantoin, typically including 1,3-dibromo-5,5-dialkylhydantoins, preferably those bearing $C_1$–$C_{10}$ alkyl groups. The alkyl groups preferably contain a total of 2–21 carbon atoms. Typical of the alkyl groups may be:

TABLE methyl
ethyl
propyls
butyls
amyls
hexyls
octyls
decyls
octadecyls etc.

The preferred hydantoin may be 1,3-dibromo-5,5-dimethylhydantoin.

In practice of the process of this invention, there may be added to a reaction mixture 84–102 parts, preferably 88–98 parts, say 93 parts of the olefin oligomer, preferably polyisobutylene, and 0.8–1.0 parts, preferably 0.85–0.95 parts, say 0.93 parts of the 1,3-dibromo-5,5-dialkyl-substituted hydantoin. The reaction mixture is maintained at 150° C.–300° C., preferably about 210° C.–245° C., say about 245° C. during the course of the reaction.

The unsaturated aliphatic dicarboxylic acid anhydride, preferably maleic acid anhydride in amount of 24.3–30 parts, preferably 26–28.4 parts, say 27 parts (corresponding to a mole ratio of 0.8:1–1:1, preferably 0.9:1–1:1, say 0.95:1) is added to the reaction mixture.

Product may be recovered in the typical case by distilling off unreacted maleic anhydride and filtering the liquified alkenyl-substituted succinic acid anhydride. The anhydride is converted to the acid by heating with water, preferably in the presence of a hydrocarbon such as xylene for 1–4, say 2 hours and then by distilling off the hydrocarbon.

One preferred material may be that formed by reaction of Indopol L-14 brand of polyisobutylene ($\overline{M}_n$ ca 335) with maleic acid anhydride. Another preferred material which may be employed as rust and corrosion inhibitor may be the reaction product of Indopol H-300 brand of polyisobutylene ($\overline{M}_n$ 1290). In each case the anhydride product is converted to acid prior to use.

It is a particular feature of this invention when the additive acid to be employed is, for example, that formed by reaction of Indopol L-14 polyisobutylene of $\overline{M}_n$ 335 and maleic acid anhydride, that salts thereof likely to be formed in the system in practice (such as the zinc salt or the calcium salt) are soluble in the system and will not cause filter plugging.

The so prepared rust and corrosion inhibitors may be added to an alkanol in minor corrosion-inhibiting amount of 0.25–25, preferably 1–20 PTB, more preferably 1–5 PTB, say 2 PTB. (PTB stands for pounds of additive per thousand barrels of alcohol or fuel). Alternatively expressed, the inhibitor may be added in amount of 0.0001–0.01 w %, preferably 0.0004–0.008 w %, more preferably 0.0004–0.002 w %, say 0.0008 w %. Larger amounts may be employed, but may not be necessary.

It is a feature of this invention that the alcohol composition so prepared is characterized by its increased corrosion and rust inhibition i.e. its decreased ability to form rust on iron surfaces in the presence of aqueous acid systems.

The corrosive nature of the formulated products may be readily measured by the Iron Strip Corrosion Test (ISCT). In this test, an iron strip (12 mm × 125 mm × 1 mm) is prepared by washing in dilute aqueous hydrochloric acid to remove mill scale, then with distilled water to remove the acid, then with acetone-followed by air drying. The strip is then polished with #100 emery cloth.

The polished strip is totally immersed in 100 ml of the test liquid in a 4 ounce bottle for 15 minutes at room temperature of 10° C. 10 ml of the test liquid is poured off and replaced with 10 ml of distilled water. The bottle is shaken the sample is maintained for 3 hours at 90° F. The percent rust on the strip is determined visually. A second reading is taken after 6 days and further readings may be taken.

The inhibited alcohols of this invention, after 40 hours of ISCT generally show a Rust and Corrosion rating below about 2–3% and frequently as low as trace-to-1%.

DESCRIPTION OF PREFERRED EMBODIMENTS

Practice of this invention will be apparent to those skilled in the art from the following examples wherein, as elsewhere in this specification, all parts are parts by weight unless otherwise specified.

EXAMPLE I

In this Example which represents practice of the best mode of carrying out the process of this invention, there may be charged to a reaction vessel 93 parts of Indopol L-14 brand of polyisobutylene ($\overline{M}_n$ 335). After purging with nitrogen, there are added 27 parts of maleic acid anhydride and, as catalyst, 1.2 parts of the Ethyl AN-702 brand of 2,2',6,6'-tetra-t-butyl dihydroxy diphenyl methane.

The reaction mixture is heated to reflux for 20 hours and then filtered and stripped of unreacted maleic acid anhydride by distillation. The Saponification number (ASTM D-94) is found to be 165 (confirmed 163).

The anhydride so prepared is converted to the acid by adding to 300 parts thereof, 300 parts of xylene and 72 parts of distilled water. This mixture is refluxed for 2 hours and stripped under vacuum to remove xylene. The product recovered is polyisobutenyl ($\overline{M}_n$ 335) succinic acid.

In this Example of the best mode of practicing the invention, the so prepared acid (19.2 parts, 5 PTB) is added as additive to 90 parts of the absolute alcohol of Table I.

Distilled water (10 parts) is added and the system is subjected to the ISCT Test. The iron strip is observed after 6 days.

EXAMPLE II

In this control example, the test procedure of Example I is duplicated except that the additive is 100 PTB of the Ethomid HT/15 brand of

wherein R is the alky radical derived from hydrogenated tallowyl—in place of the alkenyl succinic acid of Example I.

EXAMPLE III

In this control Example, no additive is present.
The results of the Iron Strip Corrosion Test were as follows:

TABLE

| Example | Six-Day Rust & Corrosion Rating |
|---|---|
| I | trace |
| II | 25%–30% |
| III | 30% |

From the above table, it will be apparent that the system of Example I, prepared in accordance with practice of this invention showed only a trace of rust and corrosion. Control Examples II–III showed 25%–30% rust and corrosion which is unsatisfactory.

Results comparable to those of Example I may be obtained when the additive is:

TABLE

| Example | Additive |
|---|---|
| IV | Polyisobutylene (derived from Indopol L-100 brand of polyisobutylene of $\overline{M}_n$ 460) succinic acid |
| V | Polyisobutylene (derived from Indopol L-10 brand of polyisobutylene of $\overline{M}_n$ 320) succinic acid |
| VI | Polyisobutylene (derived from Indopol H-35 brand of polyisobutylene of $\overline{M}_n$ 660) succinic acid |
| VII | Polyisobutylene (derived from Indopol L-50 brand of polyisobutylene of $\overline{M}_n$ 420) succinic acid |

TABLE

| Example | Alcohol |
|---|---|
| VIII | Gasohol containing 90 v % gasoline and 10 v % absolute ethanol |
| IX | Absolute ethanol |
| X | Absolute methanol |

The additives of this invention permit attainment of desirable corrosion inhibition in alcohol system in marked contrast to those falling outside the scope of the invention. Illustrative of such materials which do not function satisfactorily are the following:

TABLE

| Example | Additive |
|---|---|
| XI* | The anhydride product of Example I i.e. before it is converted to the acid product. |
| XII* | Polyisobutylene (derived from Indopol L-14 brand of polyisobutylene of $\overline{M}_n$ 345) succinic acid - as its dimethyl ester |
| XIII* | Polyisobutylene (derived from Indopol L-14 brand of polyisobutylene of $\overline{M}_n$ 345) succinic as its calcium salt |
| XIV* | Polyisobutylene (derived from Indopol L-14 brand of polyisobutylene of $\overline{M}_n$ 345) succinic as its magnesium salt |

It should also be noted that acids wherein the oligomer derived moiety has a molecular weight below about 300 and particularly below about 200, are unsatisfactory—typically because in practice they form insoluble calcium salts in contact with water and the calcium salt may exchange ions with the galvanized tank to form insoluble zinc soaps—both of which will plug filters.

In contrast, the acids of this invention derived from oligomer moieties of molecular weight $\overline{M}_n$ greater than about 300 form soluble calcium and zinc salts.

Although this invention has been illustrated by reference to specific embodiments, it will be apparent to those skilled in the art that various changes and modifications may be made which clearly fall within the scope of this invention.

What is claimed is:
1. A composition comprising
   (i) a water-soluble alcohol; and
   (ii) an effective corrosion-inhibiting amount, 0.0001–0.01 w% of, as corrosion inhibiting agent, an alkenyl-substituted aliphatic dicarboxylic acid, said alkenyl group having a molecular weight $\overline{M}_n$ of at least about 300.
2. A composition as claimed in claim 1 wherein the alkenyl substituent in said alkenyl-substituted aliphatic dicarboxylic acid is derived from an olefin having 2–8 carbon atoms.
3. A composition as claimed in claim 1 wherein the alkenyl substituent in said alkenyl-substituted aliphatic dicarboxylic acid is derived from an olefin having 2–4 carbon atoms.
4. A composition as claimed in claim 1 wherein the alkenyl substituent in said alkenyl-substituted aliphatic dicarboxylic acid is derived from butylene.
5. A composition as claimed in claim 1 wherein the alkenyl substituent has a molecular weight $M_n$ of about 300–30,000.
6. A composition as claimed in claim 1 wherein the alkenyl substituent has a molecular weight $M_n$ of about 300–3000.
7. A composition as claimed in claim 1 wherein the alkenyl substituent has a molecular weight $M_n$ of about 1050–1400.
8. A composition as claimed in claim 1 wherein said aliphatic dicarboxylic acid is a succinic acid.
9. A composition as claimed in claim 1 wherein said aliphatic dicarboxylic acid is succinic acid se.
10. A composition as claimed in claim 1 wherein said corrosion-inhibiting amount is 0.0004–0.008 w%.
11. A composition as claimed in claim 1 wherein said corrosion-inhibiting amount is 0.0004–0.002 w%.
12. A composition comprising;
   (i) at least one alcohol selected from the group consisting of methanol and ethanol; and

(ii) 0.0001–0.01 w% of polyisobutenyl ($M_n$ of at least about 300) succinic acid.

13. A composition comprising a gasohol and an effective corrosion-inhibiting amount, 0.0001–0.01 w% of, as corrosion inhibiting agent, an alkenyl ($M_n$ of at least about 300)—substituted aliphatic dicarboxylic acid.

14. The method of treating a composition containing at least one alcohol selected from the group consisting of methanol and ethanol which comprises adding to said composition containing at least one alcohol selected from the group consisting of methanol and ethanol, 0.0001–0.01 w%, as an effective corrosion-inhibiting amount, of at least one alkenyl-substituted dicarboxylic acid, said alkenyl group having a molecular weight $M_n$ of at least about 300.

15. A composition comprising
(i) a water-soluble alcohol; and
(ii) 0.0001–0.01 w%, an effective corrosion-inhibiting amount of, as the sole corrosion-inhibiting agent, an alkenyl-substituted aliphatic dicarboxylic acid, said alkenyl group having a molecular weight $\overline{M}_n$ of at least about 300.

* * * * *